United States Patent [19]

Walker et al.

[11] 4,116,677
[45] * Sep. 26, 1978

[54] N-ALKYL-ALPHA-(SUBSTITUTED PHENOXY) ALKYLAMIDES AND THEIR USE AS HERBICIDES

[75] Inventors: Francis H. Walker, Mill Valley; Don R. Baker, Orinda, both of Calif.

[73] Assignee: Stauffer Chemical Company, Westport, Conn.

[*] Notice: The portion of the term of this patent subsequent to Jul. 27, 1993, has been disclaimed.

[21] Appl. No.: 850,998

[22] Filed: Nov. 14, 1977

Related U.S. Application Data

[63] Continuation of Ser. No. 710,051, Jul. 30, 1976, abandoned.

[51] Int. Cl.² ............... A01N 9/20; C07C 103/22
[52] U.S. Cl. ........................... 71/118; 71/70; 71/76; 71/88; 71/90; 71/93; 71/100; 71/107; 71/109; 71/110; 71/116; 71/117; 71/120; 260/559 B
[58] Field of Search .............. 260/559 B; 71/118, 70, 71/76

[56] References Cited

U.S. PATENT DOCUMENTS

| 3,272,844 | 9/1966 | Easton et al. ............ 71/118 X |
| 3,439,018 | 4/1969 | Brookes et al. ............ 260/559 B |
| 3,557,209 | 1/1971 | Richter et al. ............ 71/118 X |
| 3,564,607 | 2/1971 | Breuer .................... 71/118 |
| 3,971,850 | 7/1976 | Baker et al. ............ 260/559 B |
| 4,051,184 | 9/1977 | Arneklev et al. .......... 71/118 X |

Primary Examiner—Joseph Paul Brust
Attorney, Agent, or Firm—M. Henry Heines

[57] ABSTRACT

Compounds defined by the generic formula

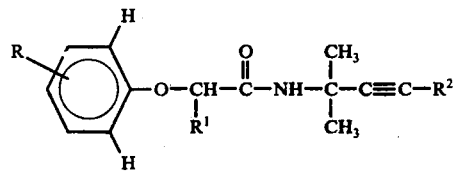

wherein
R is selected from the group consisting of trifluoromethyl, dimethyl, chloro, and dichloro,
$R^1$ is methyl or ethyl, and
$R^2$ is methyl or ethyl, exhibit herbicidal activity.

15 Claims, No Drawings

N-ALKYL-ALPHA-(SUBSTITUTED PHENOXY) ALKYLAMIDES AND THEIR USE AS HERBICIDES

This is a continuation, of application Ser. No. 710,051, filed July 30, 1976, now abandoned.

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat. Nos. 2,426,885 and its two continuations-in-part, 2,484,295 and 2,484,296. Herbicidal properties of such compounds are taught in U.S. Pat. Nos. 3,557,209, 3,272,844, 3,439,018, and 3,564,607 and Belgian Pat. No. 739,714.

BRIEF DESCRIPTION OF THE INVENTION

This invention relates to a novel class of substituted acetylenic amides and to their use as herbicides when used in a phytotoxic amount. More specifically, this invention relates to N-alkynyl-α-(substituted phenoxy) alkylamides having the formula

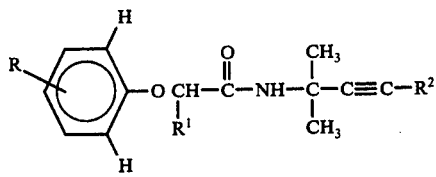

wherein R is selected from the group consisting of trifluoromethyl, dimethyl, chloro, and dichloro, and preferably R is 3,5-dimethyl or 3,5-dichloro;
$R^1$ is methyl or ethyl, preferably ethyl; and
$R^2$ is methyl or ethyl, preferably methyl.

The compounds of the present invention, as will be seen from the data which follows, have utility as both pre-emergence and post-emergence herbicides, against a wide range of plant species.

The term "herbicide", as used herein, means a compound which controls or modifies the growth of plants. By the term "herbicidally effective amount" is meant an amount of compound which causes a modifying effect upon the growth of plants. By "plants" is meant germinant seeds, emerging seedlings and established vegetation, including roots and above ground portions. Such modifying effects include all deviations from natural development, for example, killing, retardation, defoliation, desiccation, regulation, stunting, tillering, stimulation, leaf burn, dwarfing and the like.

DETAILED DESCRIPTION OF THE INVENTION

The compounds of the present invention can be prepared by the following general method, wherein R, $R^1$ and $R^2$ are as defined above:

Reaction No. 1

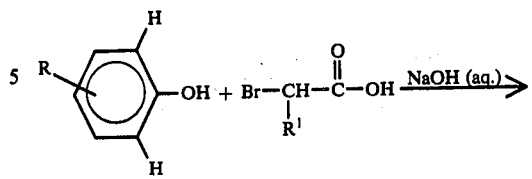

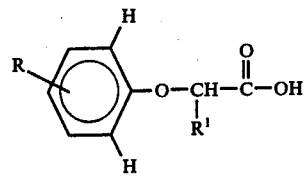

To a mixture of a molar amount of the phenol and a slight molar excess of the acid is added a slight molar excess of 50% aqueous NaOH. The product acid is then washed with suitable solvents and recovered from the organic phase.

Reaction No. 2

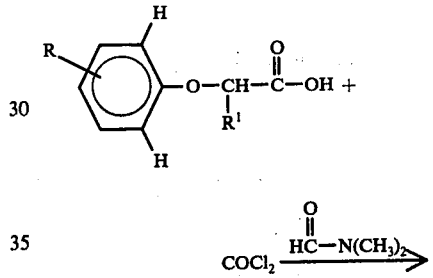

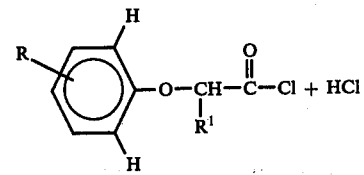

A slight molar excess of phosgene is introduced into a molar amount of the acid in a suitable solvent, to which a small amount of dimethyl formamide has been added. The excess phosgene and HCl are removed and the solvent is evaporated to leave the acid chloride. Thionyl chloride can be used as an alternative to phosgene.

Reaction No. 3

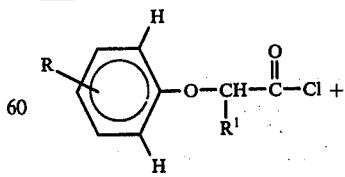

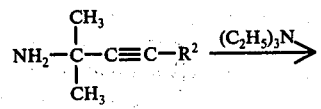

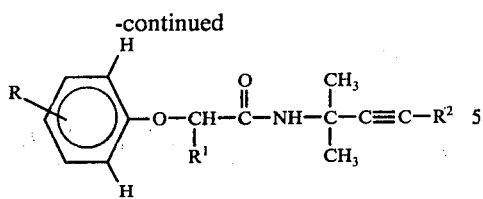

The acetylenic amine shown above can be prepared by reaction of dimethylpropargylamine with sodamide followed by reaction with an alkyl iodide or bromide. Then, according to the reaction shown above, the acid chloride is added to a solution containing both the acetylenic amine and the triethylamine at 10°–15° C. Alternatively, the reaction between the acid chloride and the acetylenic amine can be performed in the presence of aqueous caustic and toluene. After successive washings, the product is recovered from the organic phase.

As an alternative to the above general method, the following method may be used:

Reaction No. 1'

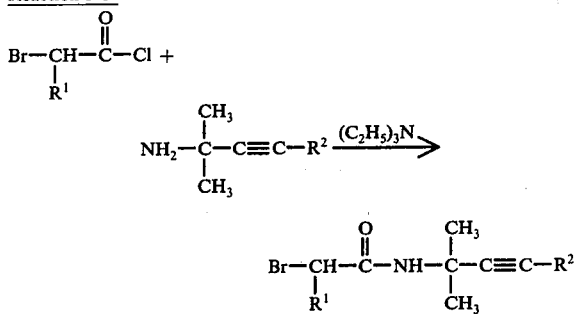

The procedure for this reaction is similar to that for Reaction No. 3 above.

Reaction No. 2'

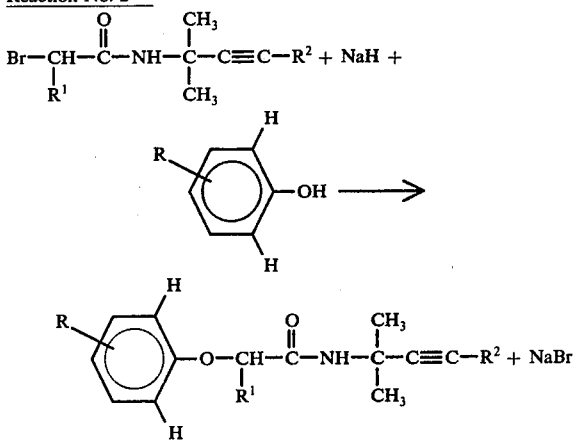

Under an inert atmosphere, a molar amount of the phenol in a suitable solvent is added to a slight molar excess of the sodium hydride suspended in the solvent. A slight molar excess of the amide, also dissolved in the solvent, is then added. After the reaction, the mixture is filtered, and the product phenoxyalkylamide is recovered from the filtrate.

The examples shown herein are illustrative of the method of preparation of the compounds of the invention.

EXAMPLE I

N-(1,1-dimethyl-2-butynyl)-2-(3,5-dimethylphenoxy)-butyramide

In a 5-liter flask were placed 244.4 g (2.0 moles) of 3,5-dimethylphenol and 400 g (2.4 moles) of 2-bromobutyric acid. The mixture was stirred and 400 g (5.0 moles) of 50% sodium hydroxide solution was added slowly with cooling so that the temperature remained below 50° C. The mixture was then heated to 115° C. for 30 minutes and 500 ml water, 500 ml perchloroethylene and 400 ml concentrated hydrochloric acid were added. The mixture was warmed to 85° C. and phase-separated. The 2-(3,5-dimethylphenoxy)-butyric acid separated on cooling to give 370 g (88.8% yield), m.p. 113°–116° C.

A mixture of 2-(3,5-dimethylphenoxy)-butyric acid [849 g (4.1 moles)], 1075 ml toluene, and 8 ml dimethylformamide was heated to 60° C. in a 5-liter flask fitted with a gas inlet tube, a stirrer, a thermometer and a dry ice condenser. Phosgene, 472 g (4.8 moles), was passed into the solution at 60°–70° C. The mixture was then heated at 60°–70° C. for thirty minutes. The dry ice condenser was then replaced with a water-cooled condenser and the solution was purged with nitrogen to remove excess phosgene and HCl. After 2 hours, purging was discontinued and the solution was vacuum stripped to leave 2-(3,5-dimethylphenoxy)butyryl chloride, 931 g (101% yield), $n_D^{30}$ 1.5050.

Liquid ammonia (1000 ml) was condensed into a 2-liter flask fitted with a dry ice condenser, a thermometer, and a glass-paddle stirrer. About 1 g of sodium was added with stirring to obtain a blue solution. Next, 0.3 g of ferric nitrate nonahydrate was added to give a light brown solution. Sodium was then added in small portions until 23.0 g (1.0 mole) had been added.

A solution of dimethylpropargyl amine, 83.1 g (1.0 mole) in 100 ml ether was added dropwise to the above solution over a period of 1 hour. An additional 100 ml ether was added, and 106 g (1.1 moles) of methyl bromide was passed into the mixture over a 90 minute period through a gas inlet-tube below the liquid surface. An additional 300 ml ether was added and after 30 minutes, the dry ice condenser was replaced with a column filled with glass helices and the ammonia was allowed to evaporate.

The residue of solid and liquid was extracted with two 100 ml portions of ether. The ether extracts were combined and filtered, and the filtrate was distilled at atmospheric pressure to a pot temperature of 71° C. The residue was vacuum distilled to give 32.4 g of liquid 4-methyl-4-amino-2-pentyne, b.p. 75°–79° C. (200 mm), $n_D^{30}$ 1.4376.

To a mixture of 102 g of 4-methyl-4-amino-2-pentyne (1.1 moles), 80 g of 50% sodium hydroxide aqueous solution (1.0 mole), 250 ml water and 1200 ml toluene, was added 227 g (1.0 mole) of 2-(3,5-dimethylphenoxy)-butyryl chloride of 25°–35° C. with rapid stirring. After 30 minutes, the mixture was washed successively with 250 ml portions of water, 10% HCl, 5% sodium carbonate solution, and water. The toluene solution was dried over magnesium sulfate and evaporated to leave a solid, 281 g, m.p. 68°–71° C. identified by NMR, mass spectrographic and infrared analyses to be N(1,1-dimethyl-2-butynyl)-2-(3,5-dimethylphenoxy)butyramide.

EXAMPLE II

N-(1,1-dimethyl-2-butynyl)-2-(3,5-dichlorophenoxy)-butyramide

The method of Example I was used with the following modifications:

The acid was made from 400 g (2.5 moles) 3,5-dichlorophenol, 501 g (3.0 moles) bromobutyric acid, and 513 g (6.4 moles) 50% aqueous NaOH, to give 498 g, m.p. 104°–110° C. (80% yield).

The acid chloride was made from 498 g (2.0 moles) of the acid, 218 g (2.2 moles) phosgene, 8 ml dimethylformamide, and 300 ml toluene, producing 550 g of a yellow liquid.

The butyramide was then made from 268 g (1.0 mole) of the acid chloride, 102 g (1.1 moles) of 4-methyl-4-amino-2-pentyne, 80 g (1.0 mole) of 50% aqueous NaOH, 250 ml water, and 1200 ml toluene, yielding 283 g (86% yield) of a solid, m.p. 99°–103° C., identified by infrared, mass spectographic, and NMR analyses as N-(1,1-dimethyl-2-butynyl)-2-(3,5-dichlorophenoxy)-butyramide.

EXAMPLE III

N-(1,1-dimethyl-2-butynyl)-2-(m-trifluoromethylphenoxy)butyramide

The method of Example I was used with the following modifications:

The acid was made from 50 g (0.3 mole) α, α, α,-trifluoro-m-cresol, 60 g (0.4 mole) 2-bromobutyric acid, and 62 g (0.77 mole) 50% aqueous NaOH. The acid was washed with 80 ml H$_2$O, 80 ml perchloroethylene and 65 ml concentrated HCl. Evaporation from perchloroethylene yielded 72 g (93% yield), m.p. 56°–64° C.

The acid chloride was made from 60 g (0.2 mole) of the acid, 33 g phosgene (0.3 mole), 2 ml dimethylformamide and 100 ml toluene. The yield was 61 g (99% yield).

The butyramide was then made from 2.9 g (0.03 mole) of 4-methyl-4-amino-2-pentyne, 3.0 g (0.03 mole) of triethylamine, and 8.0 g (0.03 mole) of the acid chloride in 100 ml methylene chloride. The product was washed with 100 ml each of water, dilute HCl, 5% Na$_2$CO$_3$ solution, and water. Evaporation from the solvent yielded 3.4 g of a solid, m.p. 65°–67° C. identified by NMR to be N-(1,1-dimethyl-2-butynyl)-2-(m-trifluoromethylphenoxy)butyramide

EXAMPLE IV

N-(1,1-dimethyl-2-butynyl)-2-(m-chlorophenoxy)-butyramide

The method of Example I was used with the following modifications:

The acid chloride was prepared from 100 g (0.8 mole) m-chlorophenol, 157 g (0.9 mole) 2-bromobutyric acid, and 160 g (2.0 moles) of 50% NaOH solution. The acid was washed with 195 ml each of H$_2$O and perchloroethylene, and 156 ml concentrated HCl. The acid separated from the perchloroethylene solution on cooling to give 90.2 g (54% yield) of a solid, m.p. 69°–70° C.

The acid chloride was made from 90 g (0.04 mole) of the acid, 50 g (0.5 mole) of phosgene, 2 ml of dimethylformamide, and 100 ml of toluene, yielding 93 g of a liquid.

The butyramide was then made from 7.3 g (0.03 mole) of the acid chloride, 2.9 g (0.03 mole) 4-methyl-4-amino-2-pentyne, 3.0 g (0.03 mole) triethylamine and 100 ml methylene chloride, yielding 8.1 g of a liquid with n$_D^{30}$ 1.5233, identified by NMR to be N-(1,1-dimethyl-2-butynyl)-2-(m-chlorophenoxy)butyramide.

Symbols g — grams
mg — milligrams
ml — milliliters
m.p. — melting point
b.p. — boiling point
n$_D^{30}$ — refractive index, sodium-D line, 30° C.
NMR — nuclear magnetic resonance In the following table, the above four examples are listed together with two additional examples which were prepared in a manner analogous to that described above, starting with the appropriate materials. The compounds in the table are representative of those embodied in the present invention.

TABLE I

| Example | COMPOUND | Melting Point or Refractive Index |
|---|---|---|
| 1 | 3,5-dimethylphenyl–O–CH(C$_2$H$_5$)–C(O)–NH–C(CH$_3$)$_2$–C≡C–CH$_3$ | 68 – 71° C |
| 2 | 3,5-dichlorophenyl–O–CH(C$_2$H$_5$)–C(O)–NH–C(CH$_3$)$_2$–C≡C–CH$_3$ | 99 – 103° C |
| 3 | m-CF$_3$-phenyl–O–CH(C$_2$H$_5$)–C(O)–NH–C(CH$_3$)$_2$–C≡C–CH$_3$ | 65 – 67° C |

TABLE I-continued

| Example | COMPOUND | Melting Point or Refractive Index |
|---|---|---|
| 4 | 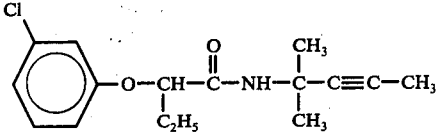 | $n_D^{30} = 1.5233$ |
| 5 | 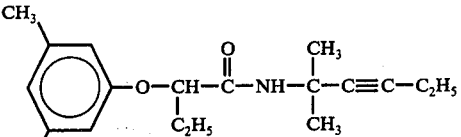 | 94 – 96° C |
| 6 | 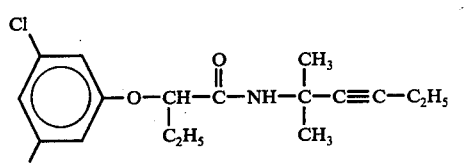 | 112.5 – 115° C |

Herbicidal Screening Test

As previously mentioned, the novel phenoxyalkyamides herein described are phytotoxic compounds which are useful and valuable in controlling various plant species. Compounds of this invention are tested as herbicides in the following manner.

Pre-emergence Herbicide Screening Test

Using an analytical balance, 20 mg of the compound to be tested is weighed out on a piece of glassine weighing paper. The paper and compound are placed in a 30 ml wide-mouth bottle and 3 ml of acetone containing 1% Tween 20 ® (an emulsifying agent defined as a polyoxyethylene sorbitan monolaurate) is added to dissolve the compound. If the material is not soluble in acetone, another solvent such as water, alcohol or dimethylformamide (DMF) is used instead. When DMF is used, only 0.5 ml or less is used to dissolve the compounds and then another solvent is used to make the volume up to 3 ml. The 3 ml of solution is sprayed uniformly on the soil contained in a small Fiber flat one day after planting weed seeds in the flat of soil. A No. 152 DeVilbiss atomizer is used to apply the spray using compressed air at a pressure of 5 lb/sq. in. The rate of application is 8 lb/acre and the spray volume is 143 gal/acre.

On the date preceding treatment, the Fiber flat, which is 7 inches long, 5 inches wide, and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), redroot pigweed (*Amaranthus retroflexus*), Indian mustard (*Brassica juncea*), curly dock (*Rumex crispus*), watergrass (*Echinochloa crusgalli*), and red oat (*Avena sativa*). Ample seeds are planted to give about 20 to 50 seedlings per row after emergence depending on the size of the plants.

After treatment, the flats are placed in the greenhouse at a temperature of 70° to 85° F. and watered by sprinkling. Two weeks after treatment the degree of injury or control is determined by comparison with untreated check plants of the same age. The injury rating from 0 to 100% is recorded for each species as percent control with 0% representing no injury and 100% representing complete kill.

Post-emergence Herbicide Screening Test

Seeds of six plant species, including hairy crabgrass, watergrass, red oat, mustard, curly dock and Pinto beans (*Phaseolus vulgaris*) are planted in the Fiber flats as described above for pre-emergence screening. The flats are produced in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg of the test compound, dissolving it in 5 ml of acetone containing 1% Tween 20 ® (an emulsifying agent defined as a polyoxyethylene sorbitan monolaurate) and then adding 5 ml of water. The solution is sprayed on the foliage using a No. 152 DeVilbiss atomizer at an air pressure of 5 lb/sq. in. The spray concentration is 0.2 and the rate is 8 lb/acre. The spray volume is 476 gal/acre. Injury ratings are recorded 14 days after treatment. The rating system is the same as described above in the pre-emergence test.

The results of these tests are shown in Table II.

TABLE II

| Compound No. | Percent Control* at 8 lb/A | |
|---|---|---|
| | Pre-Emergence | Post-Emergence |
| 1 | 99 | 66 |
| 2 | 99 | 84 |
| 3 | 91 | 83 |
| 4 | 99 | 77 |
| 5 | 88 | 61 |
| 6 | 93 | 64 |

*Average for seven plant species in the pre-emergence test and for six plant species in the post-emergence test.

The compounds of the present invention are useful as herbicides in controlling the growth of undesirable vegetation by pre-emergence or post-emergence application to the locus where control is desired. The compounds are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents, and emulsifying agents. The herbicidal formulations generally take the form of dusts, wettable powders, granules, solutions, or emulsifiable concentrates.

Dusts are free-flowing powder compositions containing the herbicidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired. The composition generally contains up to 50% of active ingredient.

Wettable powders are finely divided compositions comprising a particulate carrier impregnated with the herbicidal compound and additionally contain one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in *Pesticide Formulations* by Wade Van Valkenburg, Marcel Dekker, Inc., N.Y. 1973 at pages 79–84.

Granules comprise the herbicidal compound impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compounds can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above, employing phytotoxic or herbicidally effective amounts of the compounds described herein, are applied to the loci where control is desired in any conventional manner. The loci referred to above include soil, seeds, seedlings, and the actual plants. Dusts and liquid compositions can be applied by the use of power dusters, boom and hand sprayers and spray dusters. The compositions can also be applied from airplanes as dusts or sprays because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely be spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid, and the salts, esters and amides thereof; triazine derivatives, such as 2,4-bis(3-methoxy-propylamino)-6-methyl-thio-s-triazine; 2-chloro-4-ethylamino-6-isopropylamino-s-triazine, and 2-ethylamino-4-isopropylamino-6-methyl-mercapto-s-triazine, urea derivatives such as 3-(3,4-dichlorophenyl)-1,1-dimethyl urea, and acetamides such as N,N-di-allyl-α-chloroacetamide, N-(α-chloroacetyl) hexamethyleneimine, and N,N-diethyl-α-bromoacetamide, and the like; benzoic acids such as 3-amino-2,5-dichlorobenzoic; S-ethyl-dipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a compound of the present invention which constitutes a phytotoxic or herbicidally effective amount depends upon the nature of the seeds or plants to be controlled. The rate of application of active ingredient varies from about 0.01 to about 50 pounds per acre, with the actual amount used depending on the overall cost and the desired results. It will be readily apparent to one skilled in the art that compounds exhibiting lower herbicidal activity will require a higher dosage rate for the same degree of control than more active compounds.

What is claimed is:

1. A compound having the formula

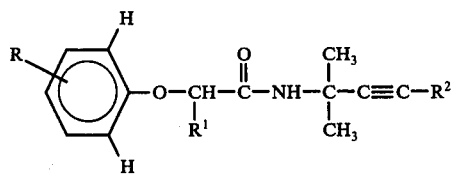

in which R is 3,5-dimethyl or 3,5-dichloro; $R^1$ is methyl or ethyl; and $R^2$ is methyl or ethyl.

2. A compound according to claim 1 in which R is 3,5-dimethyl, $R^1$ is ethyl, and $R^2$ is methyl.

3. A compound according to claim 1 in which R is 3,5-dichloro, $R^1$ is ethyl, and $R^2$ is methyl.

4. A compound according to claim 1 in which R is 3,5-dimethyl, $R^1$ is ethyl, and $R^2$ is ethyl.

5. A compound according to claim 1 in which R is 3,5-dichloro, $R^1$ is ethyl, and $R^2$ is ethyl.

6. An herbicidally active composition comprising (a) an herbicidally effective amount of a compound having the formula

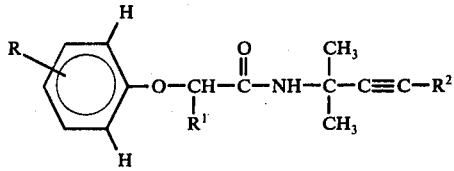

in which R is 3,5-dimethyl or 3,5-dichloro; $R^1$ is methyl or ethyl; and $R^2$ is methyl or ethyl; and (b) an inert diluent carrier.

7. The composition of claim 6 in which R is 3,5-dimethyl, $R^1$ is ethyl, and $R^2$ is methyl.

8. The composition of claim 6 in which R is 3,5-dichloro, $R^1$ is ethyl, and $R^2$ is methyl.

9. The composition of claim 6 in which R is 3,5-dimethyl, $R^1$ is ethyl, and $R^2$ is ethyl.

10. The composition of claim 6 in which R is 3,5-dichloro, $R^1$ is ethyl, and $R^2$ is ethyl.

11. A method of controlling undesirable vegetation comprising applying to the locus where control is desired an herbicidally effective amount of a compound having the formula

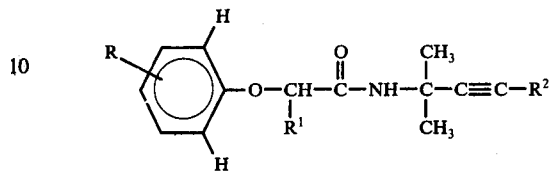

in which R is 3,5-dimethyl or 3,5-dichloro; $R^1$ is methyl or ethyl; and $R^2$ is methyl or ethyl.

12. The method of claim 11 in which R is 3,5-dimethyl, $R^1$ is ethyl, and $R^2$ is methyl.

13. The method of claim 11 in which R is 3,5-dichloro, $R^1$ is ethyl, and $R^2$ is methyl.

14. The method of claim 11 in which R is 3,5-dimethyl, $R^1$ is ethyl, and $R^2$ is ethyl.

15. The method of claim 11 in which R is 3,5-dichloro, $R^1$ is ethyl, and $R^2$ is ethyl.

* * * * *